US011154731B2

(12) United States Patent
Castiel et al.

(10) Patent No.: US 11,154,731 B2
(45) Date of Patent: *Oct. 26, 2021

(54) **COSMETIC USE OF *BIFIDOBACTERIUM* SPECIES LYSATE FOR THE TREATMENT OF DRYNESS**

(71) Applicant: L'OREAL, Paris (FR)

(72) Inventors: Isabelle Castiel, Nice (FR); Lionel Breton, Versailles (FR); Audrey Gueniche, Rueil Malmaison (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/967,657

(22) Filed: May 1, 2018

(65) Prior Publication Data

US 2018/0243590 A1 Aug. 30, 2018

Related U.S. Application Data

(63) Continuation of application No. 12/200,426, filed on Aug. 28, 2008, now abandoned.

(60) Provisional application No. 60/973,541, filed on Sep. 19, 2007.

(30) Foreign Application Priority Data

Sep. 4, 2007 (FR) ...................... 0757348

(51) Int. Cl.
| | | |
|---|---|---|
| *A61Q 19/00* | (2006.01) | |
| *A61K 8/99* | (2017.01) | |
| *A61K 35/745* | (2015.01) | |
| *A61K 8/9728* | (2017.01) | |

(52) U.S. Cl.
CPC .......... *A61Q 19/007* (2013.01); *A61K 8/9728* (2017.08); *A61K 8/99* (2013.01); *A61K 35/745* (2013.01)

(58) Field of Classification Search
CPC ...... A61Q 19/007; A61K 8/99; A61K 8/9728; A61K 35/745; A61P 43/00; A61P 17/16; A61P 17/00
See application file for complete search history.

(56) References Cited

U.S. PATENT DOCUMENTS

| | | |
|---|---|---|
| 3,156,355 A | 11/1964 | Rogers |
| 4,464,362 A | 8/1984 | Kludas et al. |
| 4,717,720 A | 1/1988 | Shroot et al. |
| 4,740,519 A | 4/1988 | Shroot et al. |
| 4,925,658 A | 5/1990 | Shroot et al. |
| 5,110,593 A | 5/1992 | Benford |
| 5,326,565 A | 7/1994 | Critchley et al. |
| 5,602,183 A | 2/1997 | Martin et al. |
| 5,605,694 A | 2/1997 | Nadaud et al. |
| 5,614,209 A | 3/1997 | Ford |
| 5,656,268 A | 8/1997 | Sorodsky |
| 5,756,088 A | 5/1998 | Matsuura et al. |
| 5,851,556 A | 12/1998 | Breton et al. |
| 5,882,665 A | 3/1999 | Meyers et al. |
| 6,139,850 A | 10/2000 | Hahn et al. |
| 6,156,335 A | 12/2000 | Rovati et al. |
| 6,156,355 A | 12/2000 | Shields, Jr. et al. |
| 6,254,886 B1 | 7/2001 | Fusca et al. |
| 6,287,553 B1 | 9/2001 | Alaluf et al. |
| 6,329,002 B1 | 12/2001 | Kim et al. |
| 6,423,325 B1 | 7/2002 | Alaluf et al. |
| 6,461,627 B1 | 10/2002 | Ichioka et al. |
| 6,506,413 B1 | 1/2003 | Ramaekers |
| 6,599,504 B1 | 7/2003 | Wadstrom et al. |
| 6,905,692 B2 | 6/2005 | Farmer |
| 7,179,460 B2 | 2/2007 | Dennin et al. |
| 7,547,527 B2 | 6/2009 | Baur et al. |
| 7,651,680 B2 | 1/2010 | Breton et al. |
| 7,651,860 B2 | 1/2010 | Howarth et al. |
| 8,101,167 B2 | 1/2012 | Gueniche |
| 8,709,454 B2 | 4/2014 | Amar et al. |
| 9,265,719 B2 | 2/2016 | Castiel et al. |
| 9,786,611 B2 | 10/2017 | Hashimoto et al. |
| 2002/0187167 A1 | 12/2002 | Vacher et al. |
| 2003/0003107 A1 | 1/2003 | Farmer |
| 2003/0039672 A1 | 2/2003 | Ginger et al. |
| 2003/0049231 A1 | 3/2003 | Baur et al. |
| 2004/0001817 A1 | 1/2004 | Giampapa |
| 2004/0013706 A1 | 1/2004 | Baur et al. |
| 2004/0029829 A1 | 2/2004 | Miyazaki et al. |
| 2004/0110270 A1 | 6/2004 | Dennin et al. |
| 2005/0106131 A1 | 5/2005 | Breton et al. |
| 2005/0180961 A1 | 8/2005 | Pecquet et al. |

(Continued)

FOREIGN PATENT DOCUMENTS

| | | |
|---|---|---|
| CN | 1136429 A | 11/1996 |
| CN | 1468105 A | 1/2004 |

(Continued)

OTHER PUBLICATIONS

McCartney, A.L. "Bifidobacteria in Foods", 2003, from Encyclopedia of Food Sciences and Nutrition, Second Edition, 2003, p. 463-470, Elsevier Science Ltd., p. 463 Only.*
Mar. 18, 2015 Office Action issued in U.S. Appl. No. 12/204,437.
May 14, 2015 Office Action issued in U.S. Appl. No. 12/200,417.
Sep. 28, 2015 Office Action issued in U.S. Appl. No. 11/241,964.
Jul. 23, 2015 Office Action issued in U.S. Appl. No. 13/514,872.
Feb. 1, 2016 Office Action issued in U.S. Appl. No. 12/200,417.
Dec. 8, 2015 Office Action issued in U.S. Appl. No. 12/204,437.
Aug. 29, 2016 Office Action issued in U.S. Appl. No. 13/514,872.
Bandyopadhyav, Debabrata, "Topical Treatment of Melasma," Indian J. Dermatol. Oct.-Dec. 2009, 54(4): 303-309.

(Continued)

*Primary Examiner* — Kade Ariani
(74) *Attorney, Agent, or Firm* — Oliff PLC

(57) ABSTRACT

Cosmetic use of an effective amount of a lysate of at least one microorganism of the genus *Bifidobacterium* species and/or one of its fractions in treating and/or preventing dryness and/or associated disorders of a keratinous substance.

9 Claims, No Drawings

(56) References Cited

U.S. PATENT DOCUMENTS

| | | |
|---|---|---|
| 2006/0002910 A1 | 1/2006 | Baur et al. |
| 2006/0008453 A1 | 1/2006 | Breton et al. |
| 2006/0018986 A1 | 1/2006 | Breton |
| 2006/0099196 A1 | 5/2006 | Breton et al. |
| 2006/0171936 A1 | 8/2006 | Gueniche et al. |
| 2006/0269508 A1 | 11/2006 | Trejo |
| 2007/0129428 A1 | 6/2007 | Richelle et al. |
| 2007/0154500 A1 | 7/2007 | Cassin et al. |
| 2008/0159970 A1 | 7/2008 | Willemin |
| 2008/0206171 A1 | 8/2008 | Gueniche |
| 2009/0068161 A1 | 3/2009 | Gueniche et al. |
| 2009/0232785 A1 | 9/2009 | Breton et al. |
| 2010/0189675 A1 | 7/2010 | Pelletier |
| 2010/0272839 A1 | 10/2010 | Gueniche et al. |
| 2010/0278793 A1 | 11/2010 | Gueniche et al. |
| 2011/0014248 A1 | 1/2011 | Castiel et al. |
| 2012/0301452 A1 | 11/2012 | Gueniche et al. |

FOREIGN PATENT DOCUMENTS

| | | |
|---|---|---|
| CN | 1635865 A | 7/2005 |
| CN | 101090706 A | 12/2007 |
| DE | 19830528 A1 | 7/1999 |
| DE | 198 06 890 A1 | 8/1999 |
| DE | 202 02 562 U1 | 5/2002 |
| EP | 0 043 128 A1 | 1/1982 |
| EP | 0 110 550 A1 | 6/1984 |
| EP | 0 199 636 A1 | 10/1986 |
| EP | 0 319 028 A1 | 6/1989 |
| EP | 0 325 540 A1 | 7/1989 |
| EP | 0 399 909 A1 | 11/1990 |
| EP | 0 402 072 A2 | 12/1990 |
| EP | 0 737 471 A2 | 10/1996 |
| EP | 0 774 249 A2 | 5/1997 |
| EP | 0 825 196 A2 | 2/1998 |
| EP | 0 852 949 A2 | 7/1998 |
| EP | 0 904 784 A1 | 3/1999 |
| EP | 0 919 226 A2 | 6/1999 |
| EP | 0 919 266 A2 | 6/1999 |
| EP | 0 931 543 A1 | 7/1999 |
| EP | 0 945 126 A2 | 9/1999 |
| EP | 1 110 555 A1 | 6/2001 |
| EP | 1 169 925 A1 | 1/2002 |
| EP | 0 806 933 B1 | 8/2002 |
| EP | 1 236 463 A1 | 9/2002 |
| EP | 1 344 528 A1 | 9/2003 |
| EP | 1 364 586 A1 | 11/2003 |
| EP | 1 374 913 A1 | 1/2004 |
| EP | 1 430 879 A2 | 6/2004 |
| EP | 1 593 382 A1 | 11/2005 |
| EP | 1 609 463 A1 | 12/2005 |
| EP | 1 642 570 A1 | 4/2006 |
| EP | 1 731 137 A1 | 12/2006 |
| EP | 2 050 434 A1 | 4/2009 |
| FR | 2 570 377 A1 | 3/1986 |
| FR | 2 738 485 A1 | 3/1997 |
| FR | 2 781 669 A1 | 2/2000 |
| FR | 2 802 088 A1 | 6/2001 |
| FR | 2 811 224 A1 | 1/2002 |
| FR | 2 848 448 A1 | 6/2004 |
| FR | 2 851 889 A1 | 9/2004 |
| FR | 2 872 047 A1 | 12/2005 |
| FR | 2 876 029 A1 | 4/2006 |
| FR | 2 877 222 A1 | 5/2006 |
| FR | 2 889 057 A1 | 2/2007 |
| FR | 2 905 856 A1 | 3/2008 |
| FR | 2 908 604 A1 | 5/2008 |
| FR | 2 912 917 A1 | 8/2008 |
| FR | 2 919 501 A1 | 2/2009 |
| JP | 2008-179601 A | 8/2008 |
| KR | 2000039570 A | 7/2000 |
| KR | 2001107152 A | 8/2000 |
| RU | 2 228 184 C2 | 5/2004 |
| RU | 2241441 C1 * | 12/2004 |
| WO | 96/19184 A1 | 6/1996 |
| WO | 99/49877 A2 | 10/1999 |
| WO | 00/49885 A1 | 8/2000 |
| WO | 00/70972 A1 | 11/2000 |
| WO | 01 13927 A2 | 3/2001 |
| WO | 01/15715 A2 | 3/2001 |
| WO | 01/17365 A1 | 3/2001 |
| WO | 01/45721 A1 | 6/2001 |
| WO | 01/97822 A1 | 12/2001 |
| WO | 02/28402 A1 | 4/2002 |
| WO | 03/057210 A1 | 7/2003 |
| WO | 03/068250 A1 | 8/2003 |
| WO | 03/070203 A1 | 8/2003 |
| WO | 03/070260 A1 | 8/2003 |
| WO | 03/071883 A1 | 9/2003 |
| WO | 03/099037 A1 | 12/2003 |
| WO | 2004/052462 A1 | 6/2004 |
| WO | 2004/112509 A2 | 12/2004 |
| WO | 2005/030230 A1 | 4/2005 |
| WO | 2005/058255 A1 | 6/2005 |
| WO | 2006/000992 A1 | 1/2006 |
| WO | 2006/037922 A1 | 4/2006 |
| WO | 2006/050768 A1 | 5/2006 |
| WO | 2007/015027 A1 | 2/2007 |
| WO | 2007/112996 A2 | 10/2007 |
| WO | 2009/031106 A2 | 3/2009 |

OTHER PUBLICATIONS

Oct. 5, 2016 Office Action issued in U.S. Appl. No. 12/200,417.
Jun. 6, 2014 Office Action issued in U.S. Appl. No. 13/514,824.
Jul. 7, 2016 Office Action Issued in U.S. Appl. No. 12/204,437.
Mar. 3, 2016 Office Action issued in CN Application No. 201410328504.6.
Manual for female body, edited by Wangshu, Chinese Zhigong Press, Edition 1, pp. 102-103, Jan. 31, 2007.
"Concentration data for Hesperidin in Orange [Blond], juice from concentrate." Phenol-Explorer, Version 3.0; available at http://www.phenol-explorer.eu/contents/graph?compound_id=207&experimental_method_group_id=2&food_id=9&unit_type=molar.
Jun. 27, 2014 Office Action issued in U.S. Appl. No. 12/204,437.
Jan. 31, 2017 Office Action issued in Korean Application No. 10-2012-7017440.
May 11, 2017 Final Rejection issued in U.S. Appl. No. 13/514,872.
Jun. 12, 2017 Non-Final OA issued in U.S. Appl. No. 12/200,417.
"Facing Facts About Acne," Webpage of the Food and Drug Administration accessible at <https://www.fda.gov/ForConsumerUpdates/ucm174521.htm>, accessed Apr. 27, 2017, published Aug. 21, 2009 according to google.
NPL pdf document "Guidance memorandum Mar. 4, 2014" accessed Mar. 27, 2014.
NPL pdf 'radiance', a screenshot of the webpage for 'radiance' at thesaurus.com (http://www.thesaurus.com/browse/radiance) accessed Sep. 25, 2014.
NPL document "Age spots", a screenprint of the webpage http://www.healthline.com/health/age-spots#Prognosis7 accessed Sep. 25, 2014.
NPL document 'CNC' screenprint of webpage or Concept Now Cosmetics at http://conceptnowcosmetics.com/YourSkin-Dry.aspx, online since Feb. 1, 2002, accessed Sep. 29, 2014.
NPL pdf document Aging changes in skin, webpage at http://www.nlm.nih.gov/medlineplus/ency/article/004014.htm, online since Feb. 1, 2001, accessed Sep. 29, 2014.
Oct. 6, 2014 Office Action issued in U.S. Appl. No. 13/514,872.
Oct. 21, 2014 Office Action issued in U.S. Appl. No. 11/241,964.
Audrey Nosbaum et al., "Allergic and irritant contact dermatitis," EJD, vol. 19, No. 4, Jul.-Aug. 2009, pp. 325-332.
Avrelija Cencic, et al., "Functional cell models of the gut and their applications in food microbiology—A review," International Journal of Food Microbiology, 2010, pp. 1-11.
Li et al.; "Contextual Regulation of Inflammation: A Duet by Transforming Growth Factor-β and Interleukin-10;" Immunity; Apr. 2008; vol. 28; pp. 168-476 (with summary).
Perkins et al.; "A noninvasive method to assess skin irritation and comprised skin conditions using simple tape adsorption of molecular markers of inflammation;" Skin Research and Technology; Nov. 2001; vol. 7, Issue 4; 2 pages.

(56) References Cited

OTHER PUBLICATIONS

Jan. 4, 2008 Office Action issued in U.S. Appl. No. 11/241,964.
Jul. 13, 2012 Office Action issued in U.S. Appl. No. 12/200,417.
Jul. 17, 2012 Office Action issued in U.S. Appl. No. 13/330,197.
U.S. Appl. No. 12/200,426, filed Aug. 28, 2008 in the name of Castiel et al.
U.S. Appl. No. 13/471,730, filed May 5, 2012 in the name of Castiel et al.
U.S. Appl. No. 13/330,197, filed Dec. 19, 2011 in the name of Breton et al.
U.S. Appl. No. 13/514,824, filed Jun. 8, 2012 in the name of Gueniche et al.
U.S. Appl. No. 13/514,872, filed Jun. 8, 2012 in the name of Gueniche et al.
Jan. 16, 2007 Search Report issued in International Patent Application No. PCT/FR2006/050768.
Apr. 15, 2008 Search Report issued in French Patent Application No. 0757348.
Nov. 17, 2009 Search Report issued in International Patent Application No. PCT/IB2009/053204.
Office Action dated May 1, 2012 in U.S. Appl. No. 12/717,438.
Mar. 28, 2013 Office Action issued in U.S. Appl. No. 13/514,824.
Apr. 10, 2013 Office Action issued in U.S. Appl. No. 13/330,197.
Apr. 30, 2013 Office Action issued in U.S. Appl. No. 13/514,872.
L.J.H. Ward et al., "Differentiation of Lactobacillus casei, Lactobacillus paracasei and Lactobacillus rhamnosus by polymerase chain reaction," Letters in Applied Microbiology, 1999, 29, pp. 90-92.
(Jing) Xin Deng Zi, "Probiotics," Jan. 1, 2004, Chemical Industry Press, Beijing, 3 pages (with 4 pages of English Translation).
Aug. 28, 2013 International Search Report issued in International Application No. PCT/IB2012/055144.
Aug. 28, 2013 Written Opinion issued in International Application No. PCT/IB2012/055144.
Apr. 14, 2014 Office Action issued in U.S. Appl. No. 11/241,964.
Schittek et al., "Dermcidin: a novel human antibiotic peptide secreted by sweat glands," published online Nov. 5, 2001, pp. 1133-1137.
Yi et al., "In Vitro antioxidant and antimicrobial activities of extract of Pericarpium Citri Reticulatae of a new Citrus cultivar and its main flavonoids," ScienceDirect, LWT 41 (2008) pp. 597-603.
Aug. 8, 2007 Office Action issued in U.S. Appl. No. 11/159,198.
Apr. 28, 2008 Office Action issued in U.S. Appl. No. 11/159,198.
Jan. 8, 2009 Office Action issued in U.S. Appl. No. 11/159,198.
Sep. 14, 2009 Notice of Allowance issued in U.S. Appl. No. 11/159,198.
May 2, 2011 Office Action issued in U.S. Appl. No. 12/204,437.
Nov. 10, 2011 Office Action issued in U.S. Appl. No. 12/204,437.
Leverkus et al., "Post-Transcriptional Regulation of UV Induced TNF-α Expression", The Society for Investigative Dermatology, Inc., 1998, pp. 353-357.
Nov. 17, 2009 International Search Report issued in International Patent Application No. PCT/IB09/053204.
Gordon et al., Mast cels as a source of both preformed and immunologically inducible TNF-α/cachectin,: Nature, vol. 346, Jul. 19, 1990, pp. 274-276, Nature Publishing Group.
Marks et al., "Arachidonic acid metabolism as a reporter of skin irritancy and target of cancer chemoprevention," Toxicology Letters, vol. 96, 1998, pp. 111-118, Elsevier.
Murphy et al., "Interlukin-1 and Cutaneous Inflammation: A Crucial Link Between Innate and Acquired Immunity," Dermatology Foundation: Progress in Dermatology, vol. 114, No. 3, Mar. 2000, pp. 602-608, The Society for Investigative Dermatology, Inc.
Larrick et al., "Activated Langrehans Cells Release Tumor Necrosis Factor," Journal of Leukocyte Biology, vol. 45, 1989, pp. 429-433, Alan R. Liss, Inc.
Groves et al., "Effect of In Vivo Interleukin-1 on Adhesion Molecule Expression in Normal Human Skin," The Journal of Investigative Dermatology, vol. 98, No. 3. Mar. 1992, pp. 384-387, The Society for Investigative Dermatology, Inc.

Holliday et al., "Differential Induction of Cutaneous TNF-α and IL-6 by Topically Applied Chemicals," American Journal of Contact Dermatitis, vol. 8, No. 3, Sep. 1997, pp. 158-164, W.B. Sanders Company.
Kalliomäki et al., "Probiotics in primary prevention of atopic disease: a randomised placebo-controlled trial," The Lancet, vol. 357, Apr. 7, 2001, pp. 1076-1079, The Lancet Publishing Group.
Isolauri et al., "Probiotics in the management of atopic eczema," Clinical and Experimental Allergy, vol. 30, 2000, pp. 1604-1610, Blackwell Science Ltd.
Nov. 9, 2009 French Search Report issued in French Patent Application No. 0951362.
Saavedra, Am J. Clinical Nutrition, 2001; 73 (suppl): 1147S-51S.
Nov. 17, 2011 Office Action issued in U.S. Appl. No. 12/717,438.
Nov. 25, 2011 Office Action issued in U.S. Appl. No. 12/200,417.
Hall et al., "The Generation of Neuronal Heterogeneity in a Rat Sensory Ganglion," The Journal of Neuroscience, vol. 17, No. 8, pp. 2775-2784, Apr. 15, 1997.
Green et al., "Measuring the Chemosensory Irritability of Human Skin," Journal of Toxicology Cutaneous and Ocular Toxicology, vol. 14, No. 1, pp. 23-48, 1995.
Sep. 19, 2011 Third Party Observation filed by the Council of Scientific & Industrial Research concerning the equivalent Canadian Patent Application CA 2 697 735 with Annex-I and Annex-II.
Ayurveda Sarasamgrahah—Shri Baidyanath Ayurveda Bhavan Limited, Calcutta, Edn. 2003 p. 485 Formulation ID: RG12/891B Formulation Name: Vijay Parpati Anupana Evam Upayoga (Exhibit 1).
Mohammed Azam Khan; Muheet Azam vol. II (Part II) (19th century AD), Matba Nizami, Kanpur, 1898 AD p. 55, Formulation ID AA26/148A1, Formulation Name: Zimaad Bara-e-kalaf (Exhibit 2).
Vagabhata; Astanga Hrdaya—(commentary by Arunadutta) edited by Bhisagacarya Harisastri Paradakara vaidya: Chaukhamba Orientalia, Varanasi, edn. 8th. 1998 [Time of origin 5th century] p. 892, Formulation ID: RS23/1719E, Formulation Name: Vyanganasaka Lepa (Exhibit 3).
Abdulla Sahib; Anuboga Vaithiya Navaneetham, Pub: Palani Thandayuthapani Devasthanam publications, Directorate of Indian systems of Medicine, Chennai. (1975). p. 91, Formulation ID: PD01/79, Formulation Name: Naga Parpam (Exhibit 4).
Ziya Al-Din Abdullah Ibn Al-Baitar; Al Jaam'e-li Mufradaat-al-Advia-wal-Aghzia, vol. IV (13th century AD), Matba Amra, Cairo, Egypt, 1874 AD p. 57, Formulation ID: MH2/93, Formulation Name: Karm-e Barri (Exhibit 5).
Smkaradajisastripade; Aryabhisaka—Gujarati Edited (Hindustana No Vaidyaraja) Translation by Harikrishna Bhagwan Lal Vyas; Sastu Sahitya Vardhaka Karyalaya, Bhadra, Ahmedabad, Edn. 12th, 1957 p. 168, Formulation ID: RG/173, Formulation Name: Draksadicurnam (05) (Exhibit 6).
Abu Alli Ibn-e-Sina; Al-Qaanoon-fil-Tibb, vol. II (11th century AD), Institute of History of Medicine and Medical Research, Jamia Hamdard, New Delhi-62, 1987 AD p. 344, Formulation ID: AHI/603A, Formulation Name: Dawa-e-Kuzbara (Exhibit 7).
Basavaraja; Basavarajiyam-Chaukhamba Sanskrit Pratisthan, Delhi; Edn. 1st Reprint; 2005 [Time of origin 15th century] p. 90, Formulation ID: VK1/176, Formulation Name: Jophesu Pathyam (Exhibit 8).
Abdulla Sahib; Anuboga Vaithiya Navaneetham, Pub: Palani Thandayuthapani Devasthanam publications, Directorate of Indian Systems of Medicine, Chennai. (1975). p. 109, Formulation ID: KS01/127, Formulation Name: Thiraatchaathi Nei-2 (Exhibit 9).
Mohammad Akbar Arzani; Qaraabaadeen Qaadri (17th century AD), Ahamadi Publication, Delhi, 1968 AD p. 3-4, Formulation ID: MH5/01, Formulation Name: Itrifal Sagheer (Exhibit 10).
Mohammad Shareef Khan; Ilaaj al-Amraaz (18th century AD), Afzal-al-Matab, Barqi Press, Delhi, 1921 AD p. 33, Formulation ID: MH1/287, Formulation Name: Majoon Mufarreh-1 (Exhibit 11).
Apr. 15, 2008 Search Report issued in French Application No. 0757352.
Jun. 20, 2008 Office Action issued in U.S. Appl. No. 11/241,964.
Jan. 13, 2009 Office Action issued in U.S. Appl. No. 11/241,964.
Jun. 4, 2009 Office Action issued in U.S. Appl. No. 11/241,964.

(56) References Cited

OTHER PUBLICATIONS

Feb. 5, 2010 Office Action issued in U.S. Appl. No. 11/241,964.
Aug. 28, 2005 Search Report issued in French Application No. 0452258.
May 18, 2011 Office Action issued in U.S. Appl. No. 12/607,142.
Dec. 13, 2011 Office Action issued in U.S. Appl. No. 12/607,142.
Pierard-Franchimont et al., International Journal of Cosmetic Science, 2002, 24, pp. 249-256.
Gupta et al., J. Am. Acad. Dermatol. 2004, 51 (5), pp. 785-798.
Kragballe, Curr. Probl. Dermatol. 2009, vol. 38, pp. 160-171.
Nov. 18, 2011 Office Action issued in U.S. Appl. No. 12/659,597.
Paragh et a;.; "Novel Sphingolipid Derivatives Promote Keratinocyte Differenciation," Experimental Dermatology, vol. 17, No. 12, Mar. 17, 2008 (pp. 1004-1016) XP002543996.
Jul. 20, 2011 Office Action issued in U.S. Appl. No. 12/685,697.
Dec. 12, 2018 Office Action issued in U.S. Appl. No. 13/514,872.
Jun. 5, 2019 Office Action issued in U.S. Appl. No. 13/514,872.
Feb. 23, 2012 Office Action issued in U.S. Appl. No. 12/685,697.
Aug. 17, 2011 Office Action issued in U.S. Appl. No. 11/989,694.
Jan. 19, 2012 Office Action issued in U.S. Appl. No. 11/989,694.
Sep. 13, 2013 Office Action issued in U.S. Appl. No. 11/989,694.
Oct. 24, 2013 Office Action issued in U.S. Appl. No. 12/204,437.
Nov. 15, 2013 Office Action issued in U.S. Appl. No. 13/514,824.
Feb. 24, 2014 Office Action issued in U.S. Appl. No. 13/056,344.
Feb. 24, 2014 Office Action issued in U.S. Appl. No. 12/607,142.
Feb. 27, 2014 Office Action issued in U.S. Appl. No. 13/514,872.
Lin et al., J. Agric. Food Chem. 1999, 47, 1460-1466.
Miyazaki et al., J. Cosmet. Sci., 55, 473-479 (Sep./Oct. 2004).
Apr. 3, 2013 Office Action issued in Chinese Application No. 201080063391.1.
Apr. 3, 2013 Office Action issued in Chinese Application No. 201080063388.X.
U.S. Appl. No. 12/717,438 in the name of Gueniche et al.
U.S. Appl. No. 11/241,964 in the name of Gueniche et al.
U.S. Appl. No. 11/989,694 in the name of Breton et al.
U.S. Appl. No. 12/204,437 in the name of Gueniche et al.
U.S. Appl. No. 12/200,417 in the name of Castiel et al.
U.S. Appl. No. 12/607,142 in the name of Gueniche et al.
U.S. Appl. No. 12/607,170 in the name of Gueniche et al.
U.S. Appl. No. 13/056,344 in the name of Castiel et al.
U.S. Appl. No. 12/659,597 in the name of Castiel et al.
U.S. Appl. No. 12/685,697 in the name of Amar et al.
U.S. Appl. No. 11/159,198 in the name of Breton et al.
Mar. 22, 2018 Office Action issued in U.S. Appl. No. 13/514,872.
Rosina Fluckiger-Isler et al. "Dietary Components of Malt Extract Such as Maltodextrins, Proteins and Inorganic Salts Have Distinct Effects on Glucose uptake and Glycogen Concentrations in Rats," 1994, J. Nutr., vol. 24, pp. 1647-1653.
Feb. 23, 2018 Office Action issued in U.S. Appl. No. 12/200,417.
Mar. 2, 2020 Office Action issued in U.S. Appl. No. 13/514,872.
"Blurry (definition)." Oxford English Dictionary Online, url: https://www.lexico.com/en/definition/blurry, retrieved Feb. 25, 2020.
Mar. 10, 2021 Office Action Issued in U.S. Appl. No. 13/514,872.

* cited by examiner

COSMETIC USE OF *BIFIDOBACTERIUM* SPECIES LYSATE FOR THE TREATMENT OF DRYNESS

This is a Continuation of application Ser. No. 12/200,426 filed Aug. 28, 2008, which claims the benefit of French Application No. 07 57348 filed on Sep. 4, 2007 and U.S. Provisional Application No. 60/973,541 filed on Sep. 19, 2007. The disclosure of the prior applications is hereby incorporated by reference herein in its entirety.

The present disclosure mainly concerns at providing a novel active principle for preventing and/or treating dryness of keratinous substances and in particular skin described as dry.

BACKGROUND

It is known that an increase in cutaneous dryness is often observed with age; however, such cutaneous dryness states may also occur in young subjects. This is because the cutaneous dryness state is a physiological state which may be present in young subjects without any pathological cause, at least apparent pathological cause. The origin of this dryness may be constitutional or acquired. Thus, many external factors can result in drying of the skin or can aggravate the state of the skin which is already dry. Mention may be made, among these factors, of difficult climatic conditions, solar radiation, or exposure to certain chemical or therapeutic agents.

Dry skin is often associated physiologically with a fall in the level of cutaneous hydration and with a detrimental change in the barrier function, measured by the imperceptible water loss. It is in particular characterized sensorially by a feeling of skin tightness and/or tension. For obvious reasons, these manifestations are sources of discomfort, indeed even of pain.

SUMMARY

There thus remains a need to have available novel active principles capable of exerting a beneficial cosmetic or therapeutic effect on the epidermis or keratinous substances in general which are described as dry. Within the meaning of the disclosure, the term "epidermis" is intended to denote both the skin and the scalp.

Unexpectedly, the Inventors have found that some probiotic microorganisms can prove to be particularly effective in the prevention and/or treatment of dry skin, with the proviso that they are employed in the form of a lysate.

Consequently, according to a first aspect, a subject-matter of the disclosure is the cosmetic use of an effective amount of a lysate of at least one microorganism of the genus *Bifidobacterium* species and/or one of its fractions for treating and/or preventing dryness and/or associated disorders of a keratinous substance, in particular dry epidermides, such as the skin or scalp.

According to another of its aspects, the present disclosure concerns the use of an effective amount of a lysate of at least one microorganism of the genus *Bifidobacterium* species and/or one of its fractions in the preparation of a composition intended to treat and/or prevent dryness and/or associated disorders of a keratinous substance.

In particular, such a composition proves to be effective in treating ichthyoses, psoriasis, hyperkeratoses, topical dermatitides and dry dandruff states of the scalp.

The present disclosure relates, according to another of its aspects, to the cosmetic use of an effective amount of a lysate of at least one microorganism of the genus *Bifidobacterium* species and/or one of its fractions in treating and/or preventing a dry dandruff state of the scalp, and more particularly dry dandruffs.

According to another of its aspect, the present disclosure concerns the use of an effective amount of a lysate of at least one microorganism of the genus *Bifidobacterium* species and/or one of its fractions in the preparation of a composition intended to treat and/or prevent a dry dandruff state of the scalp.

Within the meaning of the present disclosure, the term "to prevent" means to reduce the risk of appearance of the phenomenon concerned.

According to another of its aspects, a subject-matter of the disclosure is a method, in particular a cosmetic method, for treating and/or preventing dryness and/or associated disorders of a keratinous substance, in particular dry epidermides, such as the skin or scalp, in a subject, comprising at least one step of administration to the said subject of at least an effective amount of a lysate of at least one microorganism of the genus *Bifidobacterium* species and/or one of its fractions.

According to another of its aspects, a subject-matter of the present disclosure is a cosmetic and/or dermatological composition, of use in particular for preventing and/or treating dry keratinous substances, in particular dry epidermides, such as the skin or scalp, comprising, in a physiologically acceptable carrier, at least an effective amount of a lysate of at least one microorganism of the genus *Bifidobacterium* species and/or one of its fractions, in combination with an effective amount of at least one additional microorganism, in particular a probiotic microorganism, distinct from said lysate.

Within the meaning of the disclosure, the expression "distinct from said lysate" means that it is possible to distinguish, within the composition, either two different microorganisms or two different forms of the same microorganism. Thus, when the additional microorganism is of the genus *Bifidobacterium* species and corresponds to the same species as that representing the lysate required according to the disclosure, this additional microorganism is then present in a form other than a lysate.

According to another of its aspects, the present disclosure concerns a cosmetic and/or dermatological composition, of use in particular for preventing and/or treating dry keratinous substances, in particular dry epidermides, such as the skin or scalp, comprising, in a physiologically acceptable carrier, at least an effective amount of a lysate of at least one microorganism of the genus *Bifidobacterium* species and/or one of its fractions, in combination with an effective amount of at least one moisturizing active principle in particular as described below.

Urea and its derivatives are very particularly suitable as such.

According to an alternative embodiment of the disclosure, the lysate according to the disclosure can be administered by the oral route.

According to another alternative embodiment of the disclosure, the lysate according to the disclosure can be administered by the topical route.

As specified below, the compositions comprising it are formulated in order to be compatible with the method of administration selected.

The term "effective amount" is understood to mean, within the meaning of the present disclosure, an amount sufficient to produce the expected effect.

DETAILED DESCRIPTION OF EMBODIMENTS

Dry Skin

As indicated above, dry skin is essentially expressed by a feeling of tightness and/or tension. The skin is also rough to the touch and appears covered with squamae. When the skin is slightly dry, these squamae are profuse but not very visible to the naked eye. They becomes less numerous but increasingly visible to the naked eye when this disorder worsens.

In the scalp, the formation of such dry squamae or dandruff is symptomatic of a dry dandruff state.

With respect to the scalp, the dry dandruff states are chronic, frequent, recurring and socially disabling states. Stress and the winter period reinforce these states in the majority of the individuals. The integrity and homeostasis of the scalp are regulated by an assembly of parameters including sebum secretion and the intra-individual sensitivity.

Thus, during dandruff states of the scalp, the cutaneous barrier, its integrity and its ecological flora are unbalanced.

The skin of the scalp is irritated, and pruriginous, fragile, less hydrated and develops significant desquamation which is reflected a dry dandruff state.

A dry dandruff state is different from a greasy dandruff state.

The former is reflected in particular by the presence of white or grey squamae, dry and of small size, whereas the latter is characterized by greasy, large and yellow squamae. The origin of this cutaneous dryness can be of constitutional or acquired type.

In the case of constitutional dry skin, it is possible to distinguish two categories: pathologic skin and nonpathologic skin.

Pathologic constitutional dry skin is represented essentially by atopic dermatitis and ichthyoses. It is virtually independent of the external conditions.

Atopic dermatitis is described as associated with a deficiency in the metabolism of the lipids of the *stratum corneum* and in particular of the ceramides. This pathology presents itself in the form of a more or less chronic xerosis affecting a large expanse of the body, associated or not associated with inflammatory and pruriginous eruptions by patches.

Atopic dermatitides are also described as chronic inflammatory pathologies of the skin, often coexisting with other atopic pathologies, such as rhinitis, conjunctivitides and allergic asthma. In the majority of cases, atopic dermatitis is reflected by dry skin associated with dysfunctionings of the epidermal barrier. An increase in imperceptible water loss is nearly always encountered.

Thus, the barrier function of the skin is detrimentally affected not only on the parts affected by eczema but also with regard to noninflammatory dry skin. This detrimental change accordingly facilitates the penetration of various substances from the environment into the skin.

What is more, colonisation of the skin by *Staphylococcus aureus* strains is generally correlated with atopic dermatitis.

Ichthyoses are pathologies characterized by a genetic deficiency which affects the keratinization process at various stages. They are manifested by significant desquamation by patches.

The pathologic constitutional dry skin concerned according to the disclosure is more particularly dry skin or dry scalp of noninflammatory origin.

In the case of nonpathologic constitutional dry skin, the severity of the state of dryness can, for its part, depend on external factors. Senile skin (characterized by a general reduction in cutaneous metabolism with age), fragile skin (very sensitive to external factors and often accompanied by erythema and rosacea) and xerosis vulgaris (of probable genetic origin and manifesting itself predominantly on the face, limbs and back of the hands) come within this skin category.

In the case of acquired dry skin, the involvement of external parameters, such as exposure to chemical agents, to difficult climatic conditions, to solar radiation or alternatively certain therapeutic treatments (retinoids, for example), is determining. Under these external influences, the epidermis can then become temporarily and locally dry. This can concern any type of epidermis.

Thus, cutaneous dryness can also be induced by an exogenous stress of chemical origin, for example of peeling type, or also of mechanical origin (rubbing, shaving).

It should be remembered that a peeling operation consists essentially in applying a chemical substance to the skin with the aim of bringing about limited and controlled destruction of the epidermis and of the surface layers of the dermis in order to improve certain disorders of the appearance of the skin.

At the same time as the peelings which may be described as chemical from the viewpoint of the chemical products which they employ, a technology involving the use of ablative and nonablative laser beams has also been developed.

The first ablative laser beams, produced with pulsed or scanned $CO_2$ lasers, have the immediate effect of vaporizing (or ablating) the epidermis and often the upper part of the dermis. A strip of the underlying dermis is generally also the site of thermal injury with denaturation and contraction of the collagen. During the healing phase, reepithelization occurs starting from the hair follicles and other adnexa in addition to an upper dermal strip ("remodelling of the collagen").

The latest generation of lasers uses a system of conversion of the laser beam into a multitude of beams spaced out from one another in order to produce, on the skin, impacts spaced out from one another, thus maintaining, between the affected areas, areas of healthy skin not detrimentally changed.

For obvious reasons, peeling thus has an action which, although controlled, remains irritating with regard to the surface of the epidermis and liable to induce cutaneous dryness.

The compositions, methods and uses according to the disclosure thus prove to be very particularly effective:

in treating states of cutaneous dryness, squamous states and in particular dry dandruff states,
in treating dry skin,
in treating itching and/or tightness associated with dry skin,
in treating cutaneous disorders related to a deficiency in excretion and/or secretion of sebum,
in physiologically restoring a suitable state of hydration to the *stratum corneum,*
in treating hyposeborrhoeic dry skin,
in stimulating sebogenesis,
in preventing and/or reducing wrinkles related to cutaneous dryness,
in improving the comfort of dry skin and a dry scalp, and in particular dry dandruff states,
in combating the dull and/or lifeless appearance of the skin as a consequence of it drying out,
in treating dry keratinous fibres,
in treating skin which has been subjected to a drying exogenous stress induced by a chemical product, such as a peeling composition, for example, or induced by peeling by radiation or also induced mechanically, in particular by rubbing, for example in shaving.

When the keratinous substances are human or animal keratinous fibres, such as the hair, body hairs and/or eyelashes, the active principle under consideration according to the disclosure proves to be particularly advantageous in preventing and/or treating the expression of signs of weakness, such as, for example, the dryness which is generally reflected by a brittle aspect of the fibre. It thus makes it possible to confer a glossy appearance on the keratinous fibres, in particular on human hair and on the coats of animals.

According to one embodiment of the disclosure, a lysate of microorganisms in accordance with the disclosure is not employed as agent for inhibiting adhesion of the pathogenic flora of the skin.

Microorganisms

As specified above, the microorganisms of the genus *Bifidobacterium* species used as active principles according to the disclosure are employed in the form of a lysate.

A lysate commonly denotes a material obtained on conclusion of the destruction or dissolution of biological cells by a "cell lysis" phenomenon, thus resulting in the release of the intracellular biological constituents naturally present in the cells of the microorganism under consideration.

Within the meaning of the present disclosure, the term "lysate" is used without distinction to denote the whole of the lysate obtained by lysis of the microorganism concerned or only a fraction of the latter.

The lysate employed is thus formed all or in part of the intracellular biological constituents and of the wall and cell membrane constituents.

More specifically, it comprises the cell cytoplasmic fraction including enzymes, such as lactic acid dehydrogenase, phosphatases, phosphoketolases and transaldolases. By way of illustration, the constituents of the cell walls are in particular peptidoglycan, murein or mucopeptide and teichoic acid and the constituents of the cell membranes are compounds of glycerophospholipid.

This cell lysis can be accomplished by various technologies, such as, for example, osmotic shock, heat shock, with ultrasound, or also under mechanical stress of centrifuging type, for example.

More particularly, this lysate can be obtained according to technology described in U.S. Pat. No. 4,464,362 and in particular according to the following protocol.

The microorganism of *Bifidobacterium* species type under consideration is cultured anaerobically in an appropriate culture medium, for example according to the conditions described in the documents U.S. Pat. No. 4,464,362 and EP 43 128. When the stationary phase of the development is reached, the culture medium can be inactivated by pasteurization, for example at a temperature of 60 to 65° C. for 30 min. The microorganisms are then collected by a conventional separation technique, for example membrane filtration or centrifuging, and resuspended in a sterile physiological NaCl solution.

The lysate can be obtained by disintegrating such a medium using ultrasound in order to release therefrom the cytoplasmic fractions, the cell wall fragments and the products resulting from the metabolism. Then all the components in their natural distribution are subsequently stabilized in a weakly acidic aqueous solution.

A concentration of the order of 0.1 to 50% by weight, in particular of 1 to 20% by weight and especially of approximately 5% by weight of active material(s), with respect to the total weight of the lysate, is thus generally obtained.

The lysate can be employed in different forms, in the form of a solution or in a pulverulent form.

The microorganism belonging to the genus *Bifidobacterium* species is more particularly chosen from the species: *Bifidobacterium longum, Bifidobacterium bifidum, Bifidobacterium breve, Bifidobacterium animalis, Bifidobacterium lactis, Bifidobacterium infantis, Bifidobacterium adolescentis* or *Bifidobacterium pseudocatenulatum* and their mixtures.

The species *Bifidobacterium longum* is very particularly suitable for the disclosure.

Within the meaning of the disclosure, the term "fraction" more particularly denotes a fragment of the said microorganism which is effective in the treatment of dry epidermides by analogy with the said whole microorganism.

The product sold under the name Repair Complex CLR® by K. RICHTER GmbH, which is formed of an inactivated lysate of the species *Bifidobacterium longum*, comes within the scope of the disclosure.

The active principle forming the lysate belonging to the genus *Bifidobacterium* species can be formulated in a proportion of at least 0.0001% by weight (expressed as dry weight), in particular in a proportion of 0.001 to 20% by weight and more particularly in a proportion of 0.001 to 2% by weight, with respect to the total weight of the carrier or of the composition comprising it.

In the specific case where the microorganism(s) is (are) formulated in compositions to be administered by the oral route, the concentration of microorganism(s), in particular probiotic microorganism(s), can be adjusted so as to correspond to doses (expressed as microorganism equivalent) varying from $5 \times 10^2$ to $10^{13}$ ufc/d and in particular from $10^5$ to $10^{11}$ ufc/d.

According to an alternative form of the disclosure, this lysate is employed in combination with another microorganism.

Thus, the compositions according to the disclosure can in addition advantageously comprise at least one additional microorganism, in particular of probiotic type, and/or one of its fractions and/or one of its metabolites.

Within the meaning of the present disclosure, the term "probiotic microorganism" is understood to mean a living microorganism which, when it is consumed in an appropriate amount, has a positive effect on the health of its host, "Joint FAO/WHO Expert Consultation on Evaluation of Health and Nutritional Properties of Probiotic in Food Including Powder Milk with Live Lactic Acid Bacteria, 6 Oct. 2001", and which can in particular improve the intestinal microbial balance.

These microorganisms which are suitable for the disclosure can be chosen in particular from the Ascomycetes, such as *Saccharomyces, Yarrowia, Kluyveromyces, Torulaspora, Schizosaccharomyces pombe, Debaromyces, Candida, Pichia, Aspergillus* and *Penicillium*, bacteria of the genus *Bacteroides, Fusobacterium, Melissococcus, Propionibacterium, Enterococcus, Lactococcus, Staphylococcus, Peptostreptococcus, Bacillus, Pediococcus, Micrococcus, Leuconostoc, Weissella, Aerococcus, Oenococcus* and *Lactobacillus*, and their mixtures.

Mention may in particular be made, as Ascomycetes which are particularly suitable for the present disclosure, of *Yarrowia lipolitica* and *Kluyveromyces lactis*, as well as *Saccharomyces cerevisiae, Torulaspora, Schizosaccharamyces pombe, Candida* and *Pichia*.

Specific examples of probiotic microorganisms are *Lactobacillus acidophilus, Lactobacillus alimentarius, Lactobacillus curvatus, Lactobacillus delbruckii* subsp. *Lactis, Lactobacillus gasseri, Lactobacillus johnsonii, Lactobacillus reuteri, Lactobacillus paracasei, Lactobacillus rhamno-* sus (*Lactobacillus* GG), *Lactobacillus sake, Lactococcus lactis, Streptococcus thermophilus, Staphylococccus carnosus*, and *Staphylococcus xylosus* and their mixtures.

More particularly, they are probiotic microorganisms resulting from the group of the lactic bacteria, such as, in particular, the *Lactobacillus* species. Mention may more particularly be made, by way of illustration of these lactic bacteria, of *Lactobacillus johnsonii, Lactobacillus paracasei, Lactobacillus reuteri, Lactobacillus rhamnosus* and their mixtures.

As specified above, the additional microorganism may or may not be the same species as that forming the lysate. However, when it is the same species, it is then present in a form other than a lysate, for example in a living form.

The species which are very particularly suitable are *Lactobacillus johnsonii*, in particular the strain deposited according to the Treaty of Budapest with the Institut Pasteur (28 rue du Docteur Roux, F-75024 Paris cedex 15) under the following designation CNCM I-1225.

Generally, the compositions according to the disclosure generally comprise from 0.0001 to 20%, in particular from 0.001 to 15% and more particularly from 0.1 to 10% of one or more additional microorganisms, in particular probiotic microorganisms.

This or these microorganism(s) can be included in the compositions according to the disclosure in a living, semi-active or inactivated, or dead form.

It/they can also be included in the form of fractions of cell components. The microorganism(s) or fraction(s) can also be introduced in the form of a powder, of a liquid, of a culture supernatant or one of its fractions, diluted or undiluted, or also concentrated or nonconcentrated.

In the case where the microorganisms are formulated in a composition in a living form, the amount of living microorganisms can vary from $10^3$ to $10^{15}$ ufc/g, in particular from $10^5$ to $10^{15}$ ufc/g and more particularly from $10^7$ to $10^{12}$ ufc/g of microorganisms per gram of composition.

The compositions according to the disclosure can be provided in all the formulation forms normally available for the method of administration selected.

The carrier can be of various natures, depending on the type of composition under consideration.

As regards more particularly the compositions intended for administration by the external topical route, that is to say at the surface of a keratinous substance, such as the skin, they can be aqueous, aqueous/alcoholic or oily solutions, dispersions of the type of solutions or dispersions of the lotion or serum type, emulsions of a liquid or semi-liquid consistency of the milk type, obtained by dispersion of a fatty phase in an aqueous phase (O/W) or vice versa (W/O), or of suspensions or emulsions of the cream type, aqueous or anhydrous gels, microemulsions, microcapsules, microparticles or vesicular dispersions of ionic and/or non-ionic type.

These compositions are prepared according to the usual methods.

These compositions can in particular constitute cleansing, protecting, treating or care creams for the face, for the hands, for the feet, for the major anatomical folds or for the body (for example, day creams, night creams, make-up-removing creams, cream foundations or sun creams), make-up products, such as liquid foundations, make-up-removing milks, protective or care body milks, aftersun milks, lotions, gels or foams for caring for the skin, such as cleansing or disinfecting lotions, sun lotions, artificial tanning lotions, bath compositions, deodorant compositions comprising a bactericidal agent, aftershave gels or lotions, depilatory creams or compositions for combating insect stings and bites.

The compositions according to the disclosure can also consist of solid preparations constituting cleansing soaps or bars.

They can also be used for the scalp in the form of solutions, creams, gels, emulsions or foams or also in the form of aerosol compositions also comprising a pressurized propellant.

When the composition of the disclosure is an emulsion, the proportion of the fatty phase can range from 5 to 80% by weight and preferably from 5 to 50% by weight, with respect to the total weight of the composition. The oils, the emulsifiers and the coemulsifiers used in the composition in the form of an emulsion are chosen from those conventionally used in the cosmetic and/or dermatological field. The emulsifier and the coemulsifier can be present in the composition in a proportion ranging from 0.3 to 30% by weight and preferably from 0.5 to 20% by weight, with respect to the total weight of the composition.

When the composition of the disclosure is an oily solution or gel, the fatty phase can represent more than 90% of the total weight of the composition.

In a known way, the formulation forms intended for topical administration can also comprise adjuvants which are normal in the cosmetic, pharmaceutical and/or dermatological field, such as hydrophilic or lipophilic gelling agents, hydrophilic or lipophilic active principles, preservatives, antioxidants, solvents, fragrances, fillers, screening agents, bactericides, odour absorbers and colouring materials. The amounts of these various adjuvants are those conventionally used in the field under consideration, for example from 0.01 to 20% of the total weight of the composition. These adjuvants, depending on their nature, can be introduced into the fatty phase and/or into the aqueous phase.

Mention may be made, as fatty substances which can be used in the disclosure, of mineral oils, such as, for example, hydrogenated polyisobutene and liquid petrolatum, vegetable oils, such as, for example, a liquid fraction of shea butter, sunflower oil and apricot kernel oil, animal oils, such as, for example, perhydrosqualene, synthetic oils, in particular Purcellin oil, isopropyl myristate and ethylhexyl palmitate, unsaturated fatty acids and fluorinated oils, such as, for example, perfluoropolyethers. Use may also be made of fatty alcohols, fatty acids, such as, for example, stearic acid, and such as, for example, waxes, in particular paraffin wax, carnauba wax and beeswax. Use may also be made of silicone compounds, such as silicone oils, for example cyclomethicones and dimethicones, silicone waxes, silicone resins and silicone gums.

Mention may be made, as emulsifiers which can be used in the disclosure, for example, of glyceryl stearate, polysorbate 60, the cetearyl alcohol/oxyethylenated cetearyl alcohol comprising 33 mol of ethylene oxide mixture sold under the name Sinnowax AO® by Henkel, the PEG-6/PEG-32/Glycol Stearate mixture sold under the name Tefose® 63 by Gattefossé, PPG-3 myristyl ether, silicone emulsifiers, such as cetyl dimethicone copolyol, and sorbitan mono- or tristearate, PEG-40 stearate or oxyethylenated (20 EO) sorbitan monostearate.

Mention may be made, as solvents which can be used in the disclosure, of lower alcohols, in particular ethanol and isopropanol, or propylene glycol.

The composition of the disclosure can also advantageously comprise a thermal and/or mineral water chosen in particular from water from Vittel, water from the Vichy basin and water from La Roche Posay.

Mention may be made, as hydrophilic gelling agents, of carboxyl polymers, such as carbomer, acrylic copolymers, such as acrylate/alkylacrylate copolymers, polyacrylamides, in particular the mixture of polyacrylamide, C13-14 Isoparaffin and Laureth-7 sold under the name Sepigel 305® by SEPPIC, polysaccharides, such as cellulose derivatives, for example hydroxyalkylcelluloses, in particular hydroxypropylcellulose and hydroxyethylcellulose, natural gums, such as guar, locust bean and xanthan gums, and clays.

Mention may be made, as lipophilic gelling agents, of modified clays, such as bentones, metal salts of fatty acids, such as aluminium stearates, and hydrophobic silica, or also ethylcellulose and polyethylene.

In the case of the use of a combination in accordance with the disclosure by the oral route, use of an ingestible carrier is favoured.

Milk, yogurt, cheese, fermented milks, milk-based fermented products, ice creams, products based on fermented cereals, milk-based powders, formulas for children and infants, foodstuffs of confectionery, chocolate or cereal type, foods for animals, in particular domestic animals, tablets, including compressed tablets, hard gelatin capsules, oral supplements in a dry form and oral supplements in the liquid form are suitable in particular as dietary or pharmaceutical carriers.

Numerous embodiments of oral compositions and in particular of food supplements are possible for ingestion. They are formulated by standard processes for producing tablets, including sugar-coated tablets, capsules, including hard gelatin capsules, gels or emulsions. In particular, the active principle(s) according to the disclosure can be incorporated in any other form of food supplement or enriched food, for example food bars, or compacted or uncompacted powders. The powders can be diluted with water or in fizzy drinks, dairy products or soya derivatives or can be incorporated in food bars.

According to a specific embodiment, the additional microorganisms under consideration according to the disclosure can be formulated in compositions in an encapsulated form, so as to significantly improve their lifetime. In such a case, the presence of a capsule can in particular slow down or prevent the decomposition of the microorganism in the gastrointestinal tract.

Of course, the topical or oral compositions or the combinations according to the disclosure can additionally comprise several other active principles.

Mention may be made, as active principles conventionally employed, of vitamins B3, B5, B6, B8, C, E or PP, niacin, carotenoids, polyphenols and minerals, such as zinc, calcium, magnesium, and the like.

In particular, use may be made of an antioxidant complex comprising vitamins C and E and at least one carotenoid, in particular a carotenoid chosen from β-carotene, lycopene, astaxanthin, zeaxanthin and lutein, flavonoids, such as catechins, hesperidin, proanthocyanidins and anthocyanins.

At least one prebiotic or one mixture of prebiotics may also be involved. More particularly, these prebiotics can be chosen from oligosaccharides, produced from glucose, galactose, xylose, maltose, sucrose, lactose, starch, xylan, hemicellulose, inulin, gums of acacia type, for example, or one of their mixtures. More particularly, the oligosaccharide comprises at least one fructooligosaccharide. More particularly, this prebiotic can comprise a mixture of fructooligosaccharide and of inulin.

In the topical formulation forms, use may more particularly be made, as hydrophilic active principles, of proteins or protein hydrolysates, amino acids, polyols, in particular $C_2$ to $C_{10}$ polyols, such as glycerol, sorbitol, butylene glycol and polyethylene glycol, urea, allantoin, sugars and sugar derivatives, water-soluble vitamins, starch, or bacterial or plant extracts, such as those of aloe vera.

As regards the lipophilic active principles, use may be made of retinol (vitamin A) and its derivatives, tocopherol (vitamin E) and its derivatives, ceramides, essential oils and nonsaponifiable materials (tocotrienol, sesamin, γ-oryzanol, phytosterols, squalenes, waxes or terpenes).

According to one embodiment, a composition of the disclosure is devoid of vitamin A.

According to an alternative form of the disclosure, the lysate in accordance with the disclosure can be employed in a topical composition with an agent which is active with regard to the epidermides, in particular dry epidermides.

Mention may in particular be made, by way of illustration and without implied limitation of such active principles, of moisturizing active principles.

The term "moisturizing active principle" is understood to mean:

either a compound which influences the barrier function, for the purpose of maintaining the hydration of the *stratum corneum*, or an occlusive compound. Mention may be made of ceramides, sphingoid-based compounds, lecithins, glycosphingolipids, phospholipids, cholesterol and its derivatives, phytosterols (stigmasterol, β-sitosterol or campesterol), essential fatty acids, 1-2-diacylglycerol, 4-chromanone, pentacyclic triterpenes, petrolatum and lanolin;

or a compound which directly increases the water content of the *stratum corneum*, such as urea and its derivatives, trehalose and its derivatives, hyaluronic acid and its derivatives, glycerol, pentanediol, pidolates, serine, xylitol, lactic acid and sodium lactate, glyceryl polyacrylate, ectoine and its derivatives, chitosan, oligo- and polysaccharides, cyclic carbonates, N-lauroylpyrrolidonecarboxylic acid and N-α-benzoyl-L-arginine;

or a compound which activates the sebaceous glands, such as steroidal derivatives (including DHEA) and vitamin D and its derivatives.

These compounds can represent from 0.001% to 30% and preferably from 0.01 to 20% of the total weight of the composition according to the disclosure.

Mention may more particularly be made, by way of illustration of the urea derivatives, of the (hydroxyalkyl)urea derivatives, in particular derivatives described in the document FR 2 877 222.

Consideration may also be given, as active principles capable of being more particularly combined with the lysate in an oral formulation formula, to all the ingredients commonly used and/or authorized.

Mention may be made, by way of illustration, of vitamins, minerals, essential lipids, trace elements, polyphenols, flavonoids, phyto-oestrogens, antioxidants, such as lipoic acid and coenzyme Q10, carotenoids, prebiotics, proteins and amino acids, mono- and polysaccharides, amino sugars, phytosterols and triterpene alcohols of plant origin.

They are in particular vitamins A, C, D, E, PP and of the group B. The choice has preferably been made, among carotenoids, of β-carotene, lycopene, lutein, zeazanthin and astaxanthin. The minerals and trace elements particularly employed are zinc, calcium, magnesium, copper, iron, iodine, manganese, selenium or chromium(III). The selection is also in particular made, among polyphenols, of grape, tea, olive, cocoa, coffee, potato, blueberry, elder, strawberry, cranberry and onion polyphenols. The selection is preferably made, among phyto-oestrogens, of isoflavones in the free or glycosylated form, such as genistein, daidzein or glycitein, or lignans, in particular those of flax and Schisandra chinensis. Amino acids or the peptides and the proteins comprising them, such as taurine, threonine, cysteine, tryptophan or methionine. The lipids preferably belong to the group of the oils comprising mono- and polyunsaturated fatty acids, such as oleic, linoleic, α-linolenic, γ-linolenic or stearidonic acids, long-chain fish ω-3 fatty acids, such as EPA and DHA, or conjugated fatty acids resulting from plant or animals, such as CLAs (Conjugated Linoleic Acid).

The cosmetic treatment method of the disclosure can be employed in particular by administering the cosmetic and/or dermatological compositions or the combinations as defined above according to the usual technique for the use of these compositions. For example: applications of creams, gels, serums, lotions, make-up-removing milks or aftersun compositions to the keratinous substance, such as dry skin or hair, or application of a hair lotion to wet hair or of shampoos as regards the topical application.

The cosmetic method according to the disclosure can thus be employed by topical administration, for example daily, of the lysate under consideration according to the disclosure.

The method according to the disclosure can comprise a single administration. According to another embodiment, the administration is repeated, for example 2 to 3 times daily over a day or more and generally over a prolonged period of time of at least 4 weeks, indeed even 4 to 15 weeks, with, if appropriate, one or more periods of interruption.

In the description and in the following examples, unless otherwise indicated, the percentages are percentages by weight and the ranges of values worded in the form "between . . . and . . . " include the lower and upper limits specified. The ingredients are mixed, before they are formed, in the order and under conditions easily determined by a person skilled in the art.

The following examples are presented by way of illustration and without implied limitation of the field of the disclosure.

Example 1

| Milk for the care of dry skin of the face | % by weight |
|---|---|
| Magnesium chloride | 3.00 |
| Calcium ascorbate | 3.00 |
| *Bifidobacterium longum* lysate CLR (Repair Complex CLR ®)* | 10.00** |
| Glyceryl stearate | 1.00 |
| Cetearyl alcohol/oxyethylenated cetearyl alcohol comprising 30 mol of EO (Sinnowax AO ®, sold by Henkel) | 3.00 |
| Cetyl alcohol | 1.00 |
| Dimethicone (DC 200 Fluid ®, sold by Dow Corning) | 1.00 |
| Liquid petrolatum | 6.00 |
| Isopropyl myristate (Estol IMP 1514 ®, sold by Uniqema) | 3.00 |
| Antioxidant | 0.05 |
| Glycerol | 20.00 |
| Preservative | 0.30 |
| Water | q.s. for 100 |

*Repair Complex CLR ®, sold by K. Richter GmbH and corresponding to a formulation comprising 5% by weight of active principles
**amount expressed as total product Example 2

| Milk for the care of dry skin of the face | % by weight |
|---|---|
| Magnesium ascorbate | 3.00 |
| Blackcurrant seed oil | 4.00 |
| Borage oil | 4.00 |
| Inactivated *Lactobacillus johnsonii* powder | 5.00 |
| *Bifidobacterium longum* lysate CLR (Repair Complex CLR ®)* | 10.00** |
| Glyceryl stearate | 1.00 |
| Cetearyl alcohol/oxyethylenated cetearyl alcohol comprising 3 mol of EO (Sinnowax AO ®, sold by Henkel) | 3.00 |
| Cetyl alcohol | 1.00 |
| Dimethicone (DC 200 Fluid ®, sold by Dow Corning) | 1.00 |
| Liquid petrolatum | 6.00 |
| Isopropyl myristate (Estol IPM 1514 ®, sold by Uniqema) | 3.00 |
| Glycerol | 20.00 |
| Preservative | 0.30 |
| Water | q.s. for 100 |

*Repair Complex CLR ®, sold by K. Richter GmbH and corresponding to a formulation comprising 5% by weight of active principles
**amount expressed as total product Example 3

| Lotion for the scalp | % by weight |
|---|---|
| *Bifidobacterium longum* lysate CLR (Repair Complex CLR ®)* | 5.00** |
| Antioxidant | 0.05 |
| Isopropanol | 40.0 |
| Preservative | 0.30 |
| Water | q.s for 100 |

*Repair Complex CLR ® sold by K. Richter GmbH and corresponding to a formulation comprising 5% by weight of active principles
**amount expressed as total product Example 4

| Milk for the care of the scalp | % by weight |
|---|---|
| *Bifidobacterium longum* (lysate CLR) (Repair Complex CLR ®)* | 5.00** |
| Glyceryl stearate | 1.00 |
| Cetearyl alcohol/oxyethylenated cetearyl alcohol comprising 30 mol of EO (Sinnowax AO ®, sold by Henkel) | 3.00 |
| Cetyl alcohol | 1.00 |
| Dimethicone (DC 200 Fluid ® sold by Dow Corning) | 1.00 |
| Liquid petrolatum | 6.00 |
| Isopropyl myristate (Estol IMP 1514 ® sold by Uniqema) | 3.00 |
| Antioxidant | 0.05 |
| Preservative | 0.30 |
| Water | q.s. for 100 |

*Repair Complex CLR ® sold by K. Richter GmbH and corresponding to a formulation comprising 5% by weight of active principles
**amount expressed as total product

Example 5

| Gel for the care of the scalp | % by weight |
| --- | --- |
| *Bifidobacterium longum* (lysate CLR) (Repair Complex CLR ®)* | 5.00** |
| Hydroxypropylcellulose (Klucel H ®, sold by Hercules) | 1.00 |
| Vitamin E | 2.50 |
| Antioxidant | 0.05 |
| Isopropanol | 40.00 |
| Preservative | 0.30 |
| Water | q.s. for 100 |

*Repair Complex CLR ® sold by K. Richter GmbH and corresponding to a formulation comprising 5% by weight of active principles
**amount expressed as total product

Example 6

| Cream for the care of the scalp | % by weight |
| --- | --- |
| Arachidyl behenyl alcohol/arachidyl glucoside | 3.0 |
| Isohexadecane | 7.0 |
| *Bifidobacterium longum* (lysate CLR) (Repair Complex CLR ®)* | 5.00** |
| Glycerol | 2.0 |
| *Vitreoscilla filiformis* extract | 3.0 |
| BHT | 0.05 |
| Methyl POB | 0.1 |
| Propyl POB | 0.05 |
| Water | q.s. for 100 |

*Repair Complex CLR ® sold by K. Richter GmbH and corresponding to a formulation comprising 5% by weight of active principles
**amount expressed as total product

Example 7

| Gel for the care of the hair | % by weight |
| --- | --- |
| *Bifidobacterium longum* (lysate CLR) (Repair Complex CLR ®)* | 5.00** |
| Copper citrate | 2.00 |
| *Vitreoscilla filiformis* extract | 3.00 |
| Antioxidant | 0.05 |
| Vitamin C | 2.50 |
| Antioxidant | 0.05 |
| Isopropanol | 40.00 |
| Preservative | 0.30 |
| Water | q.s. for 100 |

*Repair Complex CLR ® sold by K. Richter GmbH and corresponding to a formulation comprising 5% by weight of active principles
**amount expressed as total product

Example 8

| Lotion for the face | % by weight |
| --- | --- |
| *Bifidobacterium longum* lysate (Repair Complex CLR ®)* | 5.00** |
| Antiinflammatory | 0.05 |
| Antioxidant | 0.05 |
| Isopropanol | 40.0 |
| Preservative | 0.30 |
| Water | q.s. for 100 |

*Repair Complex CLR ® sold by K. Richter GmbH and corresponding to a formulation comprising 5% by weight of active principles
**amount expressed as total product

Example 9

| Gel for the care of the face | % by weight |
| --- | --- |
| *Bifidobacterium longum* lysate (Repair Complex CLR ®)* | 5.00** |
| Hydroxypropylcellulose (Klucel H ®, sold by Hercules) | 1.00 |
| Vitamin E | 2.50 |
| Antioxidant | 0.05 |
| Isopropanol | 40.00 |
| Preservative | 0.30 |
| Water | q.s. for 100 |

*Repair Complex CLR ® sold by K. Richter GmbH and corresponding to a formulation comprising 5% by weight of active principles
**amount expressed as total product

Example 10

| Cream for the care of the face | % by weight |
| --- | --- |
| Arachidyl behenyl alcohol/arachidyl glucoside | 3.0 |
| Isohexadecane | 7.0 |
| *Bifidobacterium longum* lysate (Repair Complex CLR ®)* | 5.00** |
| Glycerol | 2.0 |
| *Vitreoscilla filiformis* extract | 3.0 |
| BHT | 0.05 |
| Methyl POB | 0.1 |
| Propyl POB | 0.05 |
| Water | q.s. for 100 |

*Repair Complex CLR ® sold by K. Richter GmbH and corresponding to a formulation comprising 5% by weight of active principles
**amount expressed as total product

Example 11

| Gel for the care of the face | % by weight |
| --- | --- |
| *Vitreoscilla filiformis* extract | 3.00 |
| *Bifidobacterium longum* lysate (Repair Complex CLR ®)* | 5.00** |
| Antioxidant | 0.05 |
| Vitamin C | 2.50 |
| Antioxidant | 0.05 |
| Isopropanol | 40.00 |
| Preservative | 0.30 |
| Water | q.s. for 100 |

*Repair Complex CLR ® sold by K. Richter GmbH and corresponding to a formulation comprising 5% by weight of active principles
**amount expressed as total product

Example 12

Evaluation of the Dryness of Subjects Treated with a *Bifidobacterium* Lysate.

The product tested is a *Bifidobacterium longum* lysate in disintegrated (with ultrasound) suspension in a weakly acidic aqueous medium, sold under the name Repair Complex CLR®.

The active principle was tested alone in a randomized double blind study.

Sixty-six women exhibiting dry skin were divided into two groups, placebo (n=33, group A), Repair Complex CLR® (n=33 group B). The treatments were applied topically for 58 days, the active principle being formulated at 10% of the test formulation. This carrier formulation is an Arlacel/Myrj® oil/demineralized water emulsion comprising 5% Parleam, 15% cyclopentasiloxane, 3% glycerol and 2% petrolatum.

In the placebo formulation, the absence of Repair Complex CLR® is compensated for with water.

The subjects were evaluated at D1, D29, D43 and D57. On each visit, evaluations of the dryness of the legs were carried out by the dermatologist and by self-evaluation by the subjects according to the forms specified below.

The investigating dermatologist evaluated on each visit the cutaneous dryness of the area studied (the external face of the right leg) according to a squama from 0 to 3 with regard to the following criteria: 0=skin not dry, 1=slight dryness (slight roughness), 2=moderate dryness (moderate roughness, a few squamas), 3=severe dryness (significant roughness and desquamation).

Furthermore, the investigating dermatologist, on each visit, asked the subject for a self-evaluation of the state of cutaneous dryness of her legs according to the following squama from 0 to 5: 0=not at all; 1=very slightly; 2=slightly; 3=moderately; 4=strongly; 5=very strongly.

At the same time, the change in various cutaneous markers was studied by proteomics.

A sample is withdrawn from the external face of the leg at times D1, D29, D43 and D57 by varnish stripping in order to withdraw only a portion of the *stratum corneum*, i.e. at most 4 to 5 layers of *stratum corneum*.

A 41 μm filter, type NY41 Millipore, nylon cloth (5×5 cm) is applied to a predefined area of the left leg. A transparent varnish with reference 614254/T.D., comprising: nitrocellulose 6.86 g; isopropanol 2.94 g; hypoallergenic alkyl resin 7.35 g; tributyl acetylcitrate 7.7 g; ethyl acetate 75.15 g; is then spread using a brush (15 mm) and then left to dry for 15 min. The nylon cloth is subsequently recovered using tweezers, the varnish strip being torn off with a sharp movement.

The varnish strips are stored flat at −20° C. in plastic bags.

These withdrawn samples of skin (*stratum corneum* varnish strips) were subsequently analysed by proteomics in order to evaluate the expression of various proteins according to the method described by Zieske (J. Exp. Bot., 2006, 547:1501) and Wiesse et al., (Proteomics, 2007, 7:340).

Results a) By Clinical Scoring

The forms of the score of cutaneous dryness, expressed as percentage, per visit and treatment are represented in Table 1 below. The groups are comparable at day 1 (p=0.8677).

An improvement over time is observed in both groups, which improvement is more marked for the group being treated with the topical formulation comprising 10% of Repair Complex CLR® and very particularly at D29.

TABLE 1

Clinical

| | | | | Legs | | | | |
|---|---|---|---|---|---|---|---|---|
| | | | | 0 | 1 | 2 | 3 | Total |
| A | Time | D1 | Participants | 0 | 0 | 21 | 11 | 32 |
| | | | % over time | .0% | .0% | 65.6% | 34.4% | 100.0% |
| | | D15 | Participants | 7 | 8 | 15 | 2 | 32 |
| | | | % over time | 21.9% | 25.0% | 46.9% | 6.3% | 100.0% |
| | | D29 | Participants | 4 | 18 | 7 | 1 | 30 |
| | | | % over time | 13.3% | 60.0% | 23.3% | 3.3% | 100.0% |
| | | D43 | Participants | 8 | 15 | 3 | 3 | 29 |
| | | | % over time | 27.6% | 51.7% | 10.3% | 10.3% | 100.0% |
| | | D57 | Participants | 13 | 10 | 4 | 1 | 28 |
| | | | % over time | 46.4% | 35.7% | 14.3% | 3.6% | 100.0% |
| | Total | | Participants | 32 | 51 | 50 | 18 | 151 |
| | | | % over time | 21.2% | 33.8% | 33.1% | 11.9% | 100.0% |
| B | Time | D1 | Participants | 0 | 0 | 21 | 10 | 31 |
| | | | % over time | .0% | .0% | 67.7% | 32.3% | 100.0% |
| | | D15 | Participants | 5 | 16 | 9 | 0 | 30 |
| | | | % over time | 16.7% | 53.3% | 30.0% | .0% | 100.0% |
| | | DJ29 | Participants | 8 | 19 | 3 | 0 | 30 |
| | | | % over time | 26.7% | 63.3% | 10.0% | .0% | 100.0% |
| | | D43 | Participants | 3 | 24 | 2 | 1 | 30 |
| | | | % over time | 10.0% | 80.0% | 6.7% | 3.3% | 100.0% |
| | | D57 | Participants | 11 | 15 | 4 | 0 | 30 |
| | | | % over time | 36.7% | 50.0% | 13.3% | .0% | 100.0% |
| | Total | | Participants | 27 | 74 | 39 | 11 | 151 |
| | | | % over time | 17.9% | 49.0% | 25.8% | 7.3% | 100.0% |

The reduction in the clinical score for dryness over time appears to be very significant (Chi-Square test, p<0.0001). Thus, a significant difference is observed between the groups at D29 (one-sided Chi-square test; p=0.0612) in favour of the treatment with the topical formulation comprising 10% of Repair Complex CLR®.

b) By Self-Evaluation

The forms of the score for self-evaluated cutaneous dryness, expressed as percentage, per visit and treatment are represented in Table 2 below. The groups are comparable at D1 (p=0.3945).

An improvement over time is observed in both groups, which improvement proves to be more marked for the group treated with the topical formulation comprising 10% of Repair Complex CLR®, particularly at D29, in a way comparable to what had been observed for the clinical score.

TABLE 2

|   |   | rando | | 0 | 1 | 2 | 3 | 4 | 5 | Total |
|---|---|---|---|---|---|---|---|---|---|---|
|   |   |   |   | Legs | | | | | | |
| A | Time | D1 | Participants | 0 | 0 | 2 | 9 | 15 | 6 | 32 |
|   |   |   | % over time | .0% | .0% | 6.3% | 28.1% | 46.9% | 18.8% | 100.0% |
|   |   | D15 | Participants | 2 | 11 | 6 | 11 | 2 | 0 | 32 |
|   |   |   | % over time | 6.3% | 3.4% | 18.8% | 34.4% | 6.3% | .0% | 100.0% |
|   |   | D29 | Participants | 4 | 6 | 9 | 11 | 0 | 0 | 30 |
|   |   |   | % over time | 13.3% | 20.0% | 30.0% | 36.7% | .0% | .0% | 100.0% |
|   |   | D43 | Participants | 5 | 9 | 9 | 5 | 1 | 0 | 29 |
|   |   |   | % over time | 17.2% | 31.0% | 31.0% | 17.2% | 3.4% | .0% | 100.0% |
|   |   | D57 | Participants | 6 | 7 | 9 | 5 | 1 | 0 | 28 |
|   |   |   | % over time | 21.4% | 25.0% | 32.1% | 17.9% | 3.6% | .0% | 100.0% |
|   | Total |   | Participants | 17 | 33 | 35 | 41 | 19 | 6 | 151 |
|   |   |   | % over time | 11.3% | 21.9% | 23.2% | 27.2% | 12.6% | 4.0% | 100.0% |
| B | Time | D1 | Participants | 0 | 0 | 5 | 10 | 9 | 7 | 31 |
|   |   |   | % over time | .0% | .0% | 16.1% | 32.3% | 29.0% | 22.6% | 100.0% |
|   |   | D15 | Participants | 6 | 5 | 10 | 6 | 3 | 0 | 30 |
|   |   |   | % over time | 20.0% | 16.7% | 33.3% | 20.0% | 10.0% | .0% | 100.0% |
|   |   | D29 | Participants | 8 | 9 | 7 | 5 | 1 | 0 | 30 |
|   |   |   | % over time | 26.7% | 30.0% | 23.3% | 16.7% | 3.3% | .0% | 100.0% |
|   |   | D43 | Participants | 6 | 13 | 8 | 3 | 0 | 0 | 30 |
|   |   |   | % over time | 20.0% | 43.3% | 26.7% | 10.0% | .0% | .0% | 100.0% |
|   |   | D57 | Participants | 8 | 14 | 5 | 3 | 0 | 0 | 30 |
|   |   |   | % over time | 26.7% | 46.7% | 16.7% | 10.0% | .0% | .0% | 100.0% |
|   | Total |   | Participants | 28 | 41 | 35 | 27 | 13 | 7 | 151 |
|   |   |   | % over time | 18.5% | 27.2% | 23.2% | 17.9% | 8.6% | 4.6% | 100.0% |

The groups were compared on the different visits. A significant difference is observed between the groups at D29 (one-sided Chi-square test; p=0.0561) in favour of the group treated with the topical formulation comprising 10% of Repair Complex CLR®.

c) Analysis by Proteomics

The results of the analysis by proteomics showed that the *Bifidobacterium longum* lysate stimulates the expression of various proteins which defend the epidermis from microorganisms such as the RNase 7, the dermcidin, the prolactin inducible protein (PiP), the proteins S100 A8 and A9, the histone protein of certain proteases involved in the phenomenon of desquamation (KLK7, KLK5, Cathepsin L2), while other proteins reflecting the metabolic immaturity of the cutaneous barrier see the decrease of their expression (Bleomycin hydrolase, Enolase 1, TP1, GAPDH).

The defense properties of the skin against dryness are therefore strengthened.

CONCLUSION

For the dryness of the legs (both by the clinical study and the self-evaluations), a significant reduction is observed at D29 and, overall, after 2 months, a tendency towards reduction is observed for the subjects who have been treated with the topical formulation comprising 10% of Repair Complex CLR®.

Although the present disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A cosmetic method for treating and/or preventing dry skin comprising administering to a subject an effective amount of a whole lysate of *Bifidobacterium longum*, wherein the whole lysate is obtained by ultrasonic disintegration and comprises all *B. longum* intracellular, cell wall, and cell membrane constituents, suspended in an acidic aqueous medium.

2. The method according to claim 1, in which the said whole lysate of *Bifidobacterium longum* prevents and/or reduces the wrinkles related to cutaneous dryness.

3. The method according to claim 1, in which the said whole lysate of *Bifidobacterium longum* improves comfort of dry skin and a dry scalp.

4. The method according to claim 1, in which the said whole lysate of *Bifidobacterium longum* is combats the dull and/or lifeless appearance of the skin as a consequence of it drying out.

5. The method according to claim 1, in which the said whole lysate of *Bifidobacterium longum* prevents and/or treats drying of the skin as a consequence of an application of a chemical product and/or the carrying out of a peeling or of a shaving operation.

6. The method according to claim 1, in which the said whole lysate of *Bifidobacterium longum* prevents and/or treats the expression of signs of weakness of keratinous fibres.

7. The method according to claim 1, in which the said lysate comprises from 0.1 to 50% by weight, of active material(s).

8. The method according to claim 1, in which the said lysate is administered by the topical route.

9. The method according to claim 1, in which the said lysate is administered by the oral route.

* * * * *